United States Patent [19]

Gidlund et al.

[11] Patent Number: 4,952,276
[45] Date of Patent: Aug. 28, 1990

[54] METHOD FOR MEASURING THE BLEACHING CONTENT OF PULP BLEACHING LIQUOR USING A CHEMILUMINESCENT REAGENT

[75] Inventors: Claes-Göran Gidlund, Örnsköldsvik; Håkan E. Östman, Själevad, both of Sweden

[73] Assignee: Mooch Domsjo AB, Ornskoldsvik, Sweden

[21] Appl. No.: 463,824

[22] Filed: Jan. 8, 1990

Related U.S. Application Data

[63] Continuation of Ser. No. 211,162, Jun. 22, 1988, abandoned, which is a continuation of Ser. No. 937,290, Dec. 3, 1986, abandoned.

[30] Foreign Application Priority Data

Dec. 3, 1985 [SE] Sweden .................... 8505714

[51] Int. Cl.$^5$ .................... D21C 7/12; D21C 9/10; G01N 21/76
[52] U.S. Cl. .................... 162/49; 162/62; 422/52; 422/55; 436/172
[58] Field of Search .................... 162/49, 50, 238, 61, 162/62, 263; 436/55, 52, 172; 422/55, 82, 52

[56] References Cited

U.S. PATENT DOCUMENTS

| | | | |
|---|---|---|---|
| 3,679,312 | 7/1972 | Mansberg | 436/172 |
| 3,726,599 | 4/1973 | Neary | 356/246 |
| 3,797,999 | 11/1974 | Witz et al. | 23/230 R |
| 3,962,029 | 6/1976 | Wettermark et al. | 162/49 |
| 4,013,413 | 3/1977 | Stewart et al. | 436/52 |
| 4,022,575 | 5/1977 | Hansen et al. | 436/111 |
| 4,224,304 | 9/1980 | Sawai et al. | 422/55 |
| 4,315,754 | 2/1982 | Ruzicka et al. | 422/81 |

FOREIGN PATENT DOCUMENTS

| | | | |
|---|---|---|---|
| 2142353 | 1/1973 | France . | |
| 75108035 | 8/1978 | Sweden . | |
| 1125512 | 11/1984 | U.S.S.R. | 162/49 |

OTHER PUBLICATIONS

Bublitz, "Fluorescence of Pulping Liquors: A Tool for Digester Control?", Tappi, vol. 64, No. 6, Jun. 1981.
Patent Abstracts of Japan, vol. 8, No. 52 (C-213) [1489], Mar. 9, 1984; and JP-A-58209996, (Sekisui Kagaku Kogyo K.K.), Dec. 7, 1983.
Analytical Chemistry, vol. 53, No. 8, Jul. 1981, pp. 1175-1179, Easton, Pa., U.S.; B. F. Marino et al.: "Microprocessor-Based . . . Measurements".
Analytical Chemistry, vol. 51, No. 9, Aug. 1979, pp. 1583-1585; H. R. Schroeder et al.: "Flow System for Sensitive . . . Chemiluminescence Measurements".
Analytical Chemistry, vol. 58, No. 7, Jun. 1986, pp. 1524-1527, Washington, U.S.: D. A. Hollowell et al.: "Selective Chlorine Dioxide . . . Chemiluminescent Detection".
Analytical Chemistry, vol. 52, No. 7, Apr. 1980, pp. 662-666, Ohio, U.S.; D. Pilosof et al.: "Localization . . . Chemiluminescence Cells".
Patent Abstracts of Japan, vol. 6, No. 252 (P-161) [1130], Dec. 10, 1982; & JP-A-57149950 (Horiba Seisakusho K.K.), Dec. 7, 1983.

Primary Examiner—Steve Alvo
Attorney, Agent, or Firm—Sughrue, Mion, Zinn, Macpeak & Seas

[57] ABSTRACT

A method for measuring the chemical content of bleaching liquor within the cellulose pulp industry, in which a sample of the bleaching liquor is brought together with one or more reagents, of which at least one is chemiluminescent so as to result in the emission of light, and the intensity of the light is determined as a measurement of the chemical content. The method is characterized in that a constant flow of reagent is advanced continuously through a conduit system and in that a small quantity of sample liquor is introduced sporadically or intermittently into said reagent flow so as to produce a chemiluminescent reaction, and in that the reaction, and therewith the emission of light, is caused to continue for a given period of time such that the light intensity falls within the measuring range of a light responsive device, and in that, with repeated measurements the light intensity is constantly measured after said time interval, and in that measured values of the light intensity are converted to the content of bleaching chemical.

The invention also relates to apparatus for carrying out the aforedescribed method.

15 Claims, 1 Drawing Sheet

METHOD FOR MEASURING THE BLEACHING CONTENT OF PULP BLEACHING LIQUOR USING A CHEMILUMINESCENT REAGENT

This is a continuation of application Ser. No. 211,162, filed June 22, 1988, now abandoned, which is a continuation of application Ser. No. 937,290, filed Dec. 3, 1986, now abandoned.

TECHNICAL FIELD

The present invention relates to a method for measuring the chemical content of liquors used in the bleaching of cellulose pulp. The method can be applied in conjunction with the bleaching of all cellulose pulps, irrespective of their lignin contents, i.e. including, for example, chemical pulp, chemimechanical pulp, semichemical pulp and mechanical pulp.

BACKGROUND PRIOR ART

Cellulose pulp is bleached for a number of reasons. One reason is to decrease the lignin content of the pulp, whereas in the case, for example, of chemical pulps the objective is to remove the lignin totally. Another reason for bleaching pulp is to increase its brightness. It is often endeavoured to both remove lignin from the pulp and to increase the brightness thereof.

Different bleaching agents have different effects on cellulose pulp, and can be divided into bleaching agents which remove lignin and bleaching agents which preserve the lignin. Examples of lignin removing bleaching agents include chlorine, chlorine dioxide, hypochlorite, chlorite, oxygen gas and ozone. Various kinds of peroxide, dithionite and boron hydride constitute examples of lignin preserving bleaching agents. Some of these bleaching agents possess both of the aforesaid properties. The pulp is normally treated with alkali between the various bleaching stages and washed thereafter to remove dissolved material.

A number of parameters must be taken into account when using a given bleaching agent, in order to achieve the result desired. For example, it is normally necessary to check or monitor pulp consistency, temperature, time and pH, and also preferably to control these parameters. Another important parameter is the bleaching agent content, partly of the actual bleaching liquor as such and partly subsequent to mixing the bleaching liquor with another liquid phase in the absence or presence of the pulp. There are many theories as to how a bleaching stage should be controlled. Depending upon the method of control applied, the bleaching agent content is determined immediately after mixing the agent with the pulp, at some time during the bleaching stage, or upon completion of the bleaching process. The bleaching agent is often charged to the system in excessive quantities, in which case the amount of bleaching agent that remains is normally of interest.

A relatively common method of controlling the supply of bleaching agent to the system, and therewith the amount of bleaching agent contained by the pulp suspension is one of measuring the redox potential of the suspension and of regulating the charge of bleaching agent going out from a predetermined set-point value of the redox potential, so that the set-point value is reached. In the case of bleaching chemicals, this method can only be used within a very narrow content range. In addition this particular method of measuring the redox potential in the pulp suspension is dependent on temperature, to which is added the problem of coatings on the measuring electrodes.

From the childhood of bleaching technology up to the present day, samples of bleaching agent solutions have been taken manually (and are still taken manually) at relatively wide time intervals, these samples being titrated manually, e.g. iodometrically, to arrive at a given bleaching agent content.

The samples are taken at one or more locations within the bleaching department, e.g. from the actual bleaching liquor before it is mixed into the pulp, or from the suspension liquor subsequent to mixing the bleaching liquor into the pulp, i.e. during an ongoing bleaching process, or from the suspension liquid subsequent to completion of a bleaching process, i.e. in order to determine the residual content of bleaching chemicals of the suspension liquor. This particular methodology results in poor coverage of what actually takes place during bleaching of the pulp, partly because the samples are taken at random, and partly because of the relatively long period of time that lapses from the time of taking the sample to the time at which the operator in the bleaching department receives the information concerning the content of the bleaching agent concerned.

With regard to strongly oxidative bleaching agents, such as chlorine and chlorine dioxide, it has been suggested in Swedish Patent Specification No. 7314129-3 (399 966) that samples of liquor containing these bleaching agents shall be reacted with a chemiluminescent reactant, leading to the emission of light. The total amount of light emitted is measured, and the value obtained provides data relating to the content of the bleaching agent concerned. The method in question is intended primarily for determining both the chlorine content and the chlorine dioxide content of one and the same bleaching liquor sample, which has previously been impossible to achieve to any satisfactory degree of success. This method can be applied to particular advantage in bleaching stages in which a mixture of chlorine and chlorine dioxide is used.

SUMMARY OF THE INVENTION

Technical Problem

There has been found within the cellulose pulp industry, and particularly when using strongly oxidative bleaching agents, the need for an automated method of analysis which while being reliable and requiring but little maintenance, spans a wide range of bleaching chemical concentrations, and which can be applied at relatively low costs.

Solution

The present invention satisfies this need and relates to a method for measuring the chemical content of bleaching liquor within the cellulose pulp industry, in which method a bleaching liquor sample is admixed with one or more reagents of which at least one is chemiluminescent resulting in light emission, and the intensity of the light emitted is determined as a measure of the chemical content, characterized by continuously advancing a flow of reagent through a conduit system; introducing a small quantity of sample liquid sporadically or intermittently into the flow of reagent so as to produce a chemiluminescent reaction; continuing the reaction, and therewith the emission of light, over a given period of time, so that the light intensity is such as to fall within the measuring range of a light sensitive or responsive device; constantly measuring the light intensity after said given time interval at repeated measuring operations; and converting the measured value of light intensity to the content of bleaching chemical.

The conduits used when applying the method according to the invention are preferably transparent, at least within the region thereof in which the light sensitive measuring device is located, although it is fully possible to use a conduit system in which all parts thereof are opaque. In this latter case, one end of a fibre optic cable can be connected to a non-transparent conduit system at a given location therein, while the other end of the cable can be connected to a light responsive measuring device.

According to one preferred embodiment of the invention, the reagent is supplied from a container through a conduit system which can be closed, so that substantially all unused reagent is returned to the container.

It is also preferred that the sample liquid containing the bleaching chemical concerned is delivered through a conduit system to a mixing location at which, via at least one multi-path valve, either a small amount of the sample liquor is introduced into the flow of reagent or the sample liquor is conducted beyond the flow of reagent to an outlet.

Instead of introducing the sample liquor into the reagent flow in small quantities, via a valve and a conduit loop connected thereto, the sample liquor can be introduced into the reagent flow by means of so-called hydrodynamic injection, as defined hereinafter, while using a short section of the reagent flow located in the conduit system.

That part of the reagent flow which comes into contact with the sample liquor and reacts therewith to cause light to be emitted is caused to leave the conduit system, through a sample pipe fitted with a valve, subsequent to measuring the intensity of the light emitted.

In accordance with the invention, it is also possible to take separate samples of liquor containing one or more bleaching chemicals at selected locations in the pulp mill and to introduce said samples into the reagent flow with the aid of a volumetrically graduated device. One example of such a device is a syringe provided with a cannula which can be inserted through the wall of the conduit carrying the reagent. The distance in length and/or time calculated between the location at which the sample is introduced and the location at which the intensity of the light emitted is measured must be exactly the same at each time of measuring, even in the case of the samples just mentioned.

The light responsive device with which the intensity of the light is measured, may be of any suitable known kind. In accordance with the invention, however, the device is preferably in the form of a diode capable of converting light energy into electric voltage resulting in a registerable signal. It has surprisingly been found that the output signal obtained from the diode has the form of a curve of substantially normal distribution, i.e. a so-called Gauss curve. Both the area of the curve and its peak height, i.e. the distance from the top of the curve down to its base, can be related directly to the amount in which a given bleaching chemical is present in the sample. This has been established by introducing into the aforedescribed conduit system a sample of liquor which contained a bleaching chemical of known concentration and by measuring the light intensity at a given point of time, which resulted in the printing of a curve of the aforesaid kind.

The analysis method according to the invention can be used with all bleaching agents that are capable of reacting in a chemiluminescent fashion. The invention is particularly useful for analysing bleaching liquors that contain chlorine, chlorine dioxide, hypochlorite, chlorite, or peroxide, in some form or another.

The analysis method according to the invention can be used to advantage both when manipulating actual bleaching liquors as such, for example in bleaching liquor preparation processes, and for bleaching department monitoring and/or controlling purposes.

The invention also relates to apparatus for measuring the chemical content of bleaching liquor in the cellulose pulp industry, this apparatus including means for storing a chemiluminescent reagent solution, a closed conduit system which incorporates a branch line capable of being connected to an outlet and through which the reagent solution is advanced by means of a pump means, a further conduit system for advancing a bleaching liquor sample solution with the aid of said pump means or some other pump means, and means for introducing a given quantity of sample solution into the reagent solution conduit system, by displacing the reagent solution with the sample solution, characterized in that the reagent solution conduit system has a specific length calculated from the location at which the sample solution is introduced into said system to a location in a said system at which a light responsive device measures the intensity of the light emitted as a result of a reaction between the chemiluminescent reagent solution and the sample solution containing bleaching agent.

Advantages

The method according to the invention affords a number of advantages. For example, with the aid of the invention, it is possible to determine the content of a given bleaching chemical, e.g. hydrogen peroxide, in a bleaching liquor, from small to large chemical contents, without needing to prepare the sample in any particular way, e.g. by highly diluting the sample. Another advantage is one of low chemical consumption, which enables the cost of procuring the chemicals to be kept at a low level. Even though all chemiluminescent reagents are highly expensive, calculated in kilograms for example, the fact that the conduit system according to the invention is closed means that only very small volumes of reagent will pass to the outlet. These small volumes are also ensured by the fact that in accordance with the invention it is possible to use liquor delivery pipes or hoses of very small cross-sectional area.

The actual analysis method as such has also been found to be particularly reliable. It is especially surprising that the registered curve form of the signal obtained when repeatedly taking measurements of one and the same bleaching liquor sample has a practically congruent appearance.

In addition the method according to the invention is highly flexible and has a high availability. The periodicity at which the various analyses are made can be decided upon quite readily by the operator responsible. Since the reagent solution, in accordance with a preferred embodiment of the invention, is pumped constantly around a conduit system in which no reagent solution is lost, it is possible for the temporal distance between the sampling occasions to be selected in periods which are in excess of hours and down to some tenths of a second.

DESCRIPTION OF THE BEST EMBODIMENT

Initially, preferred embodiments of the invention will be described with reference to FIGS. 1, 2 and 3, followed by a number of working examples.

Figure 1:
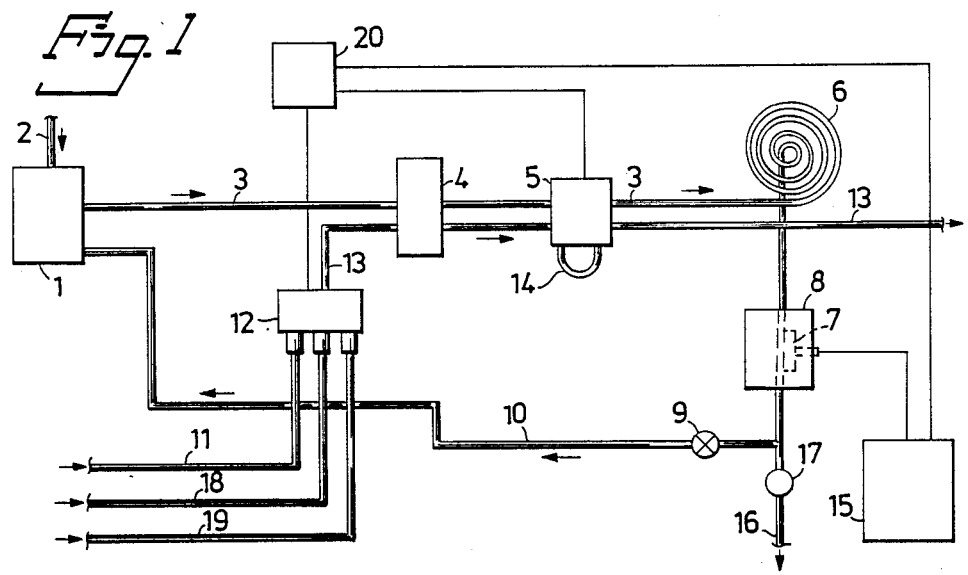
FIG. 1 illustrates an array of apparatus for carrying out a preferred embodiment of the method according to the invention.

The manner in which the method according to the invention can be applied concretely is made evident in FIG. 1. The reference 1 designates a container in which the reagent solution is stored. When necessary, further reagent solution is supplied through the conduit 2. The composition of the reagent solution may vary, although at least one of the components must always be a chemical which is chemiluminescent, i.e. a substance which reacts with certain other substances while emitting light at the same time. There are several chemiluminescent reagents which can be used in the method according to the invention. One well known substance of this kind is designated luminol. In addition to luminol, the reagent solution normally also contains copper chloride, sodium bicarbonate and sodium carbonate dissolved in water. The reagent solution is passed, via the conduit 3 and the pump 4, to two four-path valves which form a unit 5. Any known pump whatsoever may be installed at the position 4. A perstaltic pump is preferred however. When this type of pump is used, the conduit 3 may comprise a Teflon hose. It has been found in practice that a Teflon hose having a diameter of 0.7 mm functions admirably. Teflon hoses are transparent. The method according to the invention is not limited to the use of such hoses or conduits however. It is fully possible to use hoses or conduits which are not transparent. However, in this case, in accordance with a preferred embodiment of the invention, that part of the conduit or hose situated in the region where the light responsive measuring device 7 is located shall be transparent. This section of the conduit may comprise a Teflon hose or a conduit section of some other light-permeable material, such as a glass pipe. In those instances when no analysis is carried out, the pumpable reagent solution is pumped straight through the unit 5 and through the loop 6, for further transportation through the measuring device 8 incorporating a light responsive device 7 and back to the container 1, via the conduit 10 fitted with the valve 9. It is essential that the reagent solution is advanced at a constant rate of flow. It has been found, for example, that a flow rate of 2.5 ml reagent solution per minute can be used.

The sample liquor, i.e. the liquid which contains the bleaching chemical whose concentration is to be determined by analysis, is advanced by means of the pump 4 through the conduit 11, the distributing device 12 and the conduit 13 to the valve unit 5. When no analysis is carried out, the sample liquor is caused to enter the valve unit 5 on one side thereof, whereupon the liquor passes through the loop or by-pass 14 and out of the unit 5 on the opposite side thereof, for continued passage through the conduit 13 to an outlet. When the sample liquor is to be analysed, the two valves in the unit 5 are set in a manner to interrupt the flow of reagent solution through the conduit 3 by a volume (or length) which corresponds to the volume of liquid (or the length) present in the loop 14. Subsequent to introducing the sample into the conduit 3, the valves are re-set to the starting position. As a result hereof there is obtained in the conduit 3 to the right of the unit 5 a sample liquor cylinder of given length which is embraced by reaction solution on both sides thereof. As this takes place, the reaction liquor begins to penetrate and mix with the sample liquid from both sides thereof, resulting in a chemiluminescent reaction, which causes light to be emitted. It has been found difficult with the use of known light intensity meters to measure the intensity of the light in the immediate vicinity of the location at which the reagent and the bleaching chemical mix together and obtain at the same time a distinct or characteristic signal, i.e. a measurement value which correlates to a given concentration of the bleaching chemical. Consequently, tests were carried out in which the aforesaid cylinder of sample liquor was permitted to pass through a conduit loop 6 of given length to a position 8 which incorporated a measuring apparatus (e.g. in the form of a light impervious box) provided with a light responsive measuring device 7. The aforesaid length, or dimension, of the loop, or coil, is directly convertible to a given displacement in time. It has surprisingly been found that with the aid, e.g., of a photodiode placed in the immediate vicinity of the conduit within the box 8 and at a given time distance from the moment at which the sample liquor was introduced, it is possible to measure the intensity of the light emitted so as to obtain a signal in the form of a curve on the printer 15 which stands in direct relationship with the concentration of the bleaching chemical concerned in the sample liquor. The photodiode converts light to electric voltage. In order to obtain a useable curve, the measured signal is preferably amplified before being printed by the printer 15.

With regard to the aforesaid displacement in time, i.e. the time period between introducing the sample into the conduit carrying the reagent and measuring the intensity of the light emitted, this time displacement is dependent on a plurality of factors, such, as inter alia, the diameter of the conduit, the rate of flow, the volume of sample liquor. Conveniently, the chemiluminescent reaction is allowed to continued for 2–60 seconds, preferably 15–30 seconds. The most essential factor in this connection, however, is that all measurements are taken with exactly the same time extensions. The aforementioned preferred time interval is primarily applicable when analysing bleaching liquor that contains hydrogen peroxide. Consequently, in order to enable each individual bleaching agent used industrially to be analysed it is necessary to determine appropriate reaction time, prior to measuring the light intensity, with the aid of suitable tests. For example, the reaction time required for chlorine-containing bleaching agents, such as chlorine, chlorine dioxide and hypochlorite, is much shorter than that required for hydrogen peroxide.

Any suitable light responsive measuring device may be used, as an alternative to the aforesaid photodiode. Examples of such devices include phototransistors, photoresistors and photomultipliers.

The sample liquid may be advanced through the system at any desired rate of flow. The flow rate of the sample liquor is of secondary importance, since it is the volume, and then primarily the length of the loop 14, which determines the amount of sample on which the analysis is carried out. The loop 14, or shunt, is completely filled with liquor as the sample liquor is advanced, irrespective of the speed at which the sample liquor is transported. By using the same pump 4 as that used to transport the reagent solution, and the same type of hose as that used for said reagent solution, for example, a Teflon hose having a diameter of 0.7 mm, the same flow rate is also obtained, for example 2.5 ml of sample liquor per minute.

When using the aforedescribed analysis system for controlling bleaching processes, the conduit 11 is preferably connected to an arrangement of apparatus which enables a flow of sample liquor to be taken which is substantially totally free of pulp fibres. Any suitable known kind of sampling apparatus can be used. For example, there are found on the market apparatus which can be partially inserted into, for example, a conduit through which a pulp suspension containing a given bleaching agent is transported. That part of the apparatus, or device, inserted into the pulp suspension consists of a slotted tube, and part of the suspension liquor is caused to pass through the slots and into the tube for further transportation to, e.g., a buffer vessel, from which the flow of sample liquor, or individual samples of the bleaching liquor, can be taken for analysis purposes. In order to ensure that the sample liquor is totally free of fibres and also of other impurities, such as resin particles etc., it may be necessary to pass the sample liquor through a wire filter of some suitable kind.

Subsequent to taking the aforesaid measurement, the reacted chemicals are permitted to pass through the conduit 16 to an outlet. This is effected by closing the valve 9 in the conduit 10 and opening the valve 17 in the conduit 16. The valve 17 need only be held open for a very short period of time. As a result hereof the reagent solution taken from the container 1 is passed back thereto during, e.g. at least 95% of the time, resulting in extremely low consumption and therewith low reagent chemical costs.

In order to comprehend the significance of the measured signal with regard to the content of a given bleaching chemical in the sample liquor, it is necessary to calibrate the system by introducing bleaching agent solutions of known content of a given bleaching agent. It has been found advantageous to calibrate the system while using one and the same chemiluminescent bleaching agent, but in different concentrations, i.e. a solution containing the bleaching agent in a relatively low concentration and a further solution containing said bleaching agent in a relatively high concentration. These solutions are introduced into the system through the conduit 18 and the conduit 19 respectively. By measuring the peak height on the curve obtained with respective solutions and placing said peak height in relation to the known concentration in, for example, grams of bleaching agent per liter of solution, it is possible when analysing a sample containing an unknown quantity of bleaching agent, subsequent to studying the recorded curve and its peak height, to convert the signal in question to information concerning the bleaching agent content of the sample liquor in grams per liter.

The system should be calibrated at uniform time intervals, since certain discrepancies can occur in the system: Such discrepancies can be caused by aging of the hoses used in the system, which in turn affects the flow rate, the flow rate being an important parameter which must be held constant in order to achieve a satisfactory analysis result. The pump or pumps incorporated in the system must also be monitored and checked. If so desired, the analysis system illustrated in FIG. 1 can be manipulated manually, implying that the operator manually starts the pump 4, closes the valve 17 and opens the valve 9 and permits the reagent solution to circulate around the system for a short period prior to carrying out an analysis. During this period the sample is also pumped in its respective conduits through the system, via the conduit 13 to the aforesaid outlet. The valves in the valve unit 5 are re-set at a selected point in time, so as to temporarily interrupt transportation of the reagent solution and to introduce the content of the loop or shunt 14 into the conduit 3 so that the chemiluminescent reaction commences. Subsequent to transporting the aforesaid determined volume of sample liquor through the loop or coil 6 and past the photodiode 7, during simultaneous reaction with the reagent and the resultant emission of light, the valve 17 is opened and the valve 9 is closed for a brief period of time, in order to transport consumed chemicals to the outlet through the conduit 16.

It is assumed that the arrangement of apparatus illustrated in FIG. 1 will enable the sample liquor to be transported continuously to the outlet over longer or shorter periods of time. It is quite possible, however, in accordance with the present invention to supply individual samples of the bleaching liquor, optionally over relatively long intervals of time. When the invention is applied in this manner, it may be suitable to use two pumps at the location 4, a first pump for continuously transporting a constant flow of reagent solution, as described above, and a second pump, together with an associated conduit system, for transporting the optionally limited volume of sample liquor that is available. The amount of sample liquor on which the analysis is carried out is also determined in this case by the length of the loop 14 (and a conduit area which possibly deviates from that of the conduit 3).

In accordance with one preferred embodiment of the invention, the analysis system is controlled by a minicomputer 20, instead of being controlled manually. The minicomputer can be programmed specifically to control, for example, which of the liquors carried in the conduits 11, 18 or 19 shall be transported through the system. The minicomputer can also be programmed to control the positions of the valves in the valve unit 5, and it is also possible to program the computer to read the peak heights of the light intensity curve printed in the printer 15. The computer is readily capable of converting the measured signal to the corresponding correct concentration in, for example, grams per liter of the bleaching agent concerned. Thus, the minicomputer can be programmed to ensure that samples are analysed at given time intervals, for example every third or fifth minute, and to ensure that a calibration is made at given time intervals, for example each 60th minute.

Figure 2:
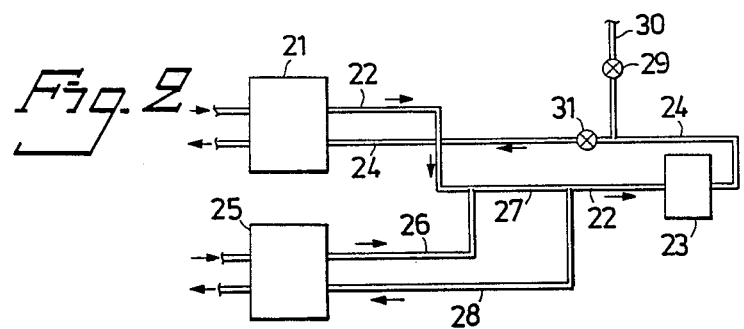
FIG. 2 illustrates an alternative method for introducing sample liquor into the reagent liquor conduit system.

FIG. 2 illustrates and alternative method of introducing the sample to the advancing reagent solution when carrying out the method according to the invention.

The reagent solution is transported through the conduit 22 for example with the aid of peristaltic pump 21, to the light measuring device 23, for further transportation through the conduit 24 back to the reagent solution container (not shown). The sample liquor can be transported, for example by means of a peristaltic pump 25, through the conduit 26 to a part 27 of the conduit 22, which is common to both conduit systems, and from there back through the conduit 28.

When no analysis is to be carried out, the valve 29 in the sampling conduit 30 is closed and the valve 31 open, which means that the reagent solution is caused, by means of the pump 21, to circulate in a constant flow in the closed system incorporating, inter alia, the conduits 22, 27 and 24. When the sample liquor is to be analysed, the pump 21 is stopped and the pump 25 started up. The sample liquor is transported to the conduits 26, 27 and 28 for a period of time of such long duration as to positively ensure that all the reagent solution within the conduit section 27 has been replaced with sample liquor. A suitable time in this respect is from 10 to 20 seconds. The pump 25 is then stopped and the pump 21 started up. As this takes place, the sample is pressed in the conduit section 27 to the right of the reagent solution while simultaneously introducing the chemiluminescent reaction caused by penetration of reagent solution from both sides of the cylindrical body of sample liquor, the length of this cylinder corresponding to the length of the conduit section 27. There is no risk of the sample liquor escaping via the conduit 28, since this conduit is already filled with stationary liquor. Thus, the sample liquor is forced to the right by means of the pump 21, through the conduit 22 and to the light intensity measuring device 23. In reality, that part of the conduit 22 located between the conduit section 27 and the measuring device 23 is considerably longer than illustrated in FIG. 2 and preferably incorporates a loop or coil, similar to that referenced 6 in FIG. 1. Subsequent to measuring the intensity of the light emitted, the consumed chemicals are caused to leave the system through the outlet, via the sampling conduit 30 and the valve 29. The valve 31 is kept closed while this takes place.

The desired quantity of sample liquor to be analysed is determined by the selected length of the conduit section 27. The method of supplying the sample illustrated in FIG. 2 is designated hydrodynamically injection.

Figure 3:
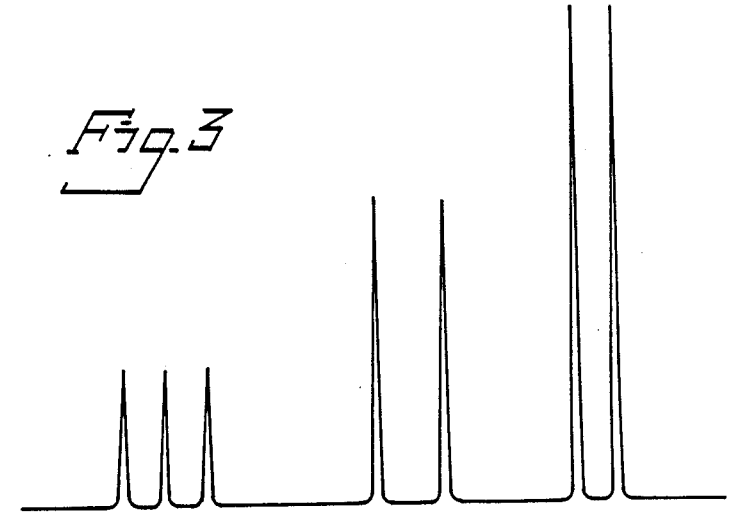
FIG. 3 illustrates an example of the measuring signal recorded in curveform when practising a preferred embodiment of the invention.

FIG. 3 illustrates an example of the signal which can be detected when carrying out the analysis method according to the invention. The illustrated curves were obtained when analysing a chemiluminescent bleaching agent while using the analysis system illustrated in FIG. 1. The intensity of the light emitted was measured by means of photodiode. As a result of the chemiluminescent reactions light is emitted within the visible wavelength range. Photodiodes responsive to light within the wavelength of 420–675 nanometers are suitable for use when practising the invention. By positioning the photodiode in the immediate vicinity of the conduit and allowing the photodiode to convert the transmitted light to a voltage it is possible, with the aid of an amplifying unit, to record the measurement signal in the form of the curves illustrated in FIG. 3. The tests were carried out on three mutally different bleaching liquors, i.e. bleaching liquors containing one and the same bleaching agent, but in three different concentrations.

With regard to the bleaching agent having the lowest concentration, three tests were carried with the analysis system at three minute intervals. These tests correspond to the three curves shown on the left of the Figure. It will be seen that the three curves are practically fully congruent. Both the surface of the curve and the peak height thereof can be used as a measurement of the amount of bleaching chemical present in the sample. The peak height has been found that most suitable parameter for use in practice. Duplicated measurements have been made on bleaching liquors containing higher qualities of bleaching chemical, and surprising conformity was also obtained in this case in the appearance of both the measured curves in respective tests. The curves illustrated in FIG. 3 have a markedly narrow configuration, i.e. the curves have a small base in relation to their height. The appearance of the curve is dependent to a large extent on the speed to which the printer 15 is set. Since the height has been found to be the parameter of primary interest, a low printer speed was selected in order to economise on printing paper. It has been found that when the printer speed is increased, the curves present a substantially normal distribution configuration. The configuration of the curve deviates from a strictly normal distribution primarily due to a delay of the signal with respect to the right-hand curve half, i.e. the right-hand curve half is not a complete mirror image of the left-hand curve half.

The fact that when practising the method according to the invention such readily readable signals are obtained as evidenced by the curves in FIG. 3 is surprising. The reason why this is so is not known. One possible explanation may be that when the mixture of the sample liquor and the reagent (i.e. the part of the sample liquor which remains in a non-reacted state subsequent to moving through the long transport path up to the measuring location) reaches the measuring apparatus 8 light of a certain intensity is still emitted and that when this light enters the measuring field of the photodiode recording of the signal begins, while the signal increases the more centrally the light emitted is located in the centre of the measuring field of the photodiode, and conversely decreases in pace with the light emission as it approaches the other end of the measuring field, and finally terminates completely as it leaves the field. This explanation is purely theoretical and has not been confirmed scientifically.

EXAMPLE 1

The present invention can be used particularly for analysing various types of peroxides, such as hydrogen peroxide for example.

The following tests were carried out in order to ascertain the reliability of the method according to the invention. A reagent solution having the following composition was prepared.

| | |
|---|---|
| 1 part luminol | 0.015 M dissolved in 0.1 M NaOH |
| 0.1 part copper chloride | 0.02 M |
| 1 part carbonate buffer | 33.2 g $Na_2CO_3$ + 53.2 g $NaHCO_3$ per liter |
| 4 parts water | |

This reagent solution was used when carrying out analysis with the use of the arrangement of apparatus illustrated in FIG. 1. The analysis system was calibrated partly with the aid of a hydrogen peroxide solution, which contained 4 grams per liter, and partly with the aid of a hydrogen peroxide solution which contained 18 grams per liter. Samples of bleaching liquor were then pumped from a full scale cellulose pulp bleaching department. The bleaching liquors contained varying quantities of hydrogen peroxide and were transported through the conduit 11, the distributing unit 12, the conduit 13 and the loop or shunt 14, up to the unit 5, where they were introduced into the conduit 3 through which the reagent solution was transported. 20 microliters of sample liquor were used in the analysis, this quantity corresponding to the volume of the loop 14. When the sample arrived at the photodiode 7, the intensity of the light emitted was measured and the recorded signal converted into grams of hydrogen peroxide per liter, in the aforedescribed manner.

The conduits 3, 11, 13 and 14 used in the tests comprised Teflon hose having an internal diameter of 0.7 mm. A peristaltic pump was used in location 4, which gave a flow rate of 2.5 ml/min, both in respect of the reagent solution and of the sample solution. The reaction time was 27 seconds, i.e. the time from introducing the sample solution into the conduit 3 at location 5 in the form of an elongated liquid cylinder and embraced on both short sides or endwalls by the reagent solution, to the time of measuring the light intensity by means of the photodiode 7.

In addition to analysing the various bleaching liquors in accordance with the invention, the liquors were also subjected to iodometric titration.

The results obtained in respective analyses are set forth in Table 1 below.

TABLE 1

| Sample Number | Iodometric titration g $H_2O_2$/l | Analysis according to the invention g $H_2O_2$/l |
|---|---|---|
| 1 | 15.5 | 15.5 |
| 2 | 10.6 | 10.2 |
| 3 | 14.0 | 14.1 |
| 4 | 12.4 | 12.5 |

It will be seen that good agreement was obtained between the measuring results achieved in accordance with the invention and the results obtained with the conventional, manual iodometric titration processes long used in practice.

It is important to note that when practising the method according to the invention it is possible to obtain data concerning the hydrogen peroxide contents of a bleaching liquor both rapidly and directly, even when the content is comparatively high. This has previously presented a problem.

Peroxides, such as hydrogen peroxide, are a common bleaching agent used when bleaching mechanical and chemimechanical pulps in particular. Various suggestions have been put forward as to how such bleaching processes should be carried out. One suggestion proposes that a bleaching agent solution containing a large quantity of hydrogen peroxide is mixed rapidly into the pulp at a relatively low pulp consistency, whereafter the pulp is pressed to a relatively high pulp consistency.

The liquid pressed from the pulp, which liquor still contains a relatively large amount of hydrogen peroxide, is recycled and mixed with freshly supplied pulp subsequent to adding further hydrogen peroxide, i.e. fresh hydrogen peroxide. This bleaching method involves the constant manipulation of liquors that contain large quantities of hydrogen peroxide, and since this chemical is expensive it is highly desirable that the hydrogen peroxide content of the liquors can be determined correctly and quickly. The analysis method according to the invention satisfies precisely this desideratum.

The method according to the invention can be applied equally as well with other types of peroxides, including organic peroxides. Excellent results are also achieved when the analysis method according to the invention is applied in conjunction with bleaching processes which use other strongly oxidative bleaching agents, such as bleaching agent solutions that contain chlorine, chlorine dioxide, hypochlorite etc.

We claim:

1. A method for measuring the bleaching chemical content of cellulose pulp bleaching liquor within the cellulose pulp industry, in which a sample of the bleaching liquor is brought together with one or more reagents, of which at least one is chemiluminescent so as to result in the emission of light, the intensity of which is determined as a measurement of said chemical content, said method comprising the steps of: continuously advancing a constant flow of reagent through a conduit system and introducing a small quantity of sample liquor intermittently into the flow of reagent, so as to produce a chemiluminescent reaction; causing the reaction, and therewith the emission of light, to continue over a given period of time of at least two seconds until the light intensity has reached its highest intensity and is decreasing so as to fall within the measuring range of a light responsive device; with repeated measurements, constantly measuring the light intensity after said given time period using said light responsive device; and converting the light intensity to the bleaching chemical content.

2. A method according to claim 1, wherein conduits forming said conduit system are transparent, at least at that part of the system at which the light responsive measuring device is located.

3. A method according to claims 1 or 2, wherein the reagent is advanced from a container through a returning conduit system for returning substantially all unused reagent to the container.

4. A method according to claim 3, wherein the sample liquor is advanced in the conduit system to a mixing location at which, via at least one multipath valve, either a small quantity of the sample liquor is introduced into the flow of reagent or said sample liquor is conducted past the flow of reagent to an outlet.

5. A method according to claim 3, wherein the sample liquor is advanced to a mixing location at which a small amount of the sample liquor is hydrodynamically injected into the flow of reagent.

6. A method according to claim 3, wherein that part of the reagent flow combined with the sample liquor and caused to react therewith is caused to leave the conduit system, via a sample conduit provided with valve means, subsequent to measuring the intensity of the light emitted.

7. A method according to claim 3, wherein the amount of sample liquor introduced is controlled by utilizing a given length of the conduit system where the reagent solution is displaced by advancing the sample solution.

8. A method according to claim 3, wherein an individual sample of the bleaching liquor is introduced into the flow of reagent.

9. A method according to claim 3, wherein the intensity of said light is measured by means including a diode for converting light energy to an electric voltage resulting in a registered signal.

10. A method according to claim 9, wherein the signal is registered in the form of a curve of substantially normal distribution; and in that the distance from the peak of the curve to the base thereof is measured and used as a direct measurement of the chemical content of the sample subsequent to comparison with the result achieved with liquors having a known chemical content.

11. A method according to claim 1 wherein the reagent is supplied from a container, and after measuring the light intensity, the reagent is advanced through the conduit system to an outlet for a predetermined period of time, and at other times, the reagent is advanced through the conduit system to the container.

12. A method according to claim 1 wherein said light intensity is outside the measuring range of the light responsive device until at least the expiration of the given period of time.

13. A method according to claim 1, wherein the given period is at least fifteen seconds.

14. A method according to claim 13, wherein the given period is no greater than sixty seconds.

15. A method according to claim 1, wherein the sample liquor is intermixed with said reagent by disposing the sample liquor in said conduit system, and subsequently flowing said reagent adjacent to each side of the sample liquor in said conduit system, and allowing said reagent to penetrate and mix with said sample liquor from each side thereof.

* * * * *